(12) United States Patent
Du et al.

(10) Patent No.: US 12,733,996 B2
(45) Date of Patent: Sep. 15, 2026

(54) COMPOUND CONTINUUM ROBOT FOR SKULL BASE TUMOR RESECTION AND CONTROL METHOD THEREFOR

(71) Applicant: SHANDONG UNIVERSITY, Jinan (CN)

(72) Inventors: Fuxin Du, Jinan (CN); Gang Zhang, Jinan (CN); Shaowei Xue, Jinan (CN); Hangxing Wei, Jinan (CN); Jing Su, Jinan (CN)

(73) Assignee: SHANDONG UNIVERSITY, Jinan (CN)

( * ) Notice: Subject to any disclaimer, the term of this patent is extended or adjusted under 35 U.S.C. 154(b) by 497 days.

(21) Appl. No.: 18/212,329

(22) Filed: Jun. 21, 2023

(65) Prior Publication Data

US 2023/0404687 A1 Dec. 21, 2023

(30) Foreign Application Priority Data

Jun. 21, 2022 (CN) ......................... 202210703784.9

(51) Int. Cl.
*A61B 34/30* (2016.01)
*A61B 17/29* (2006.01)
*A61B 34/00* (2016.01)

(52) U.S. Cl.
CPC .............. *A61B 34/30* (2016.02); *A61B 17/29* (2013.01); *A61B 34/71* (2016.02)

(58) Field of Classification Search
CPC ......... A61B 34/30; A61B 34/71; A61B 17/29; A61B 2017/00309; A61B 2034/301; A61B 2034/305
See application file for complete search history.

(56) References Cited

FOREIGN PATENT DOCUMENTS

| | | | | |
|---|---|---|---|---|
| CN | 113303914 A | * | 8/2021 | ....... A61B 17/32002 |
| WO | WO-2018174226 A1 | * | 9/2018 | ............ A61B 34/71 |

OTHER PUBLICATIONS

Du et al., CN113303914A (Aug. 27, 2021) English language metadata, abstract, and claim 1 from PE2E, Clarivate. (Year: 2021).*

(Continued)

*Primary Examiner* — Kathleen S Holwerda
*Assistant Examiner* — Cherie M Poland
(74) *Attorney, Agent, or Firm* — Oliff PLC

(57) ABSTRACT

A compound continuum robot for skull base tumor resection and a control method therefor. The robot includes a fixed base module, and a continuum mechanism, a notched continuum control mechanism, a concentric tube driving mechanism and a forceps opening and closing control mechanism which are arranged on the fixed base module. The continuum mechanism is sequentially composed of a concentric tube continuum mechanism and a notched continuum mechanism from interior to exterior, a bending motion and a rotating motion of the notched continuum mechanism are controlled by the notched continuum control mechanism, feeding and rotating motions of the concentric tube continuum mechanism are controlled by the concentric tube driving mechanism, and feeding and rotating motions of a forceps opening and closing control mechanism steel cable are controlled by the forceps opening and closing control mechanism, such that forceps are opened or closed.

14 Claims, 4 Drawing Sheets

(56) References Cited

OTHER PUBLICATIONS

Du et al., CN113303914A (Aug. 27, 2021) English language Bibliographic data, Abstract from Global Dossier/ESPACENET (Year: 2021).*
CN113303914A (Aug. 27, 2021) English translation of Chinese publication from Google Patents. (Year: 2021).*
CN113303914A (Aug. 27, 2021) PDF from Google Patents—Full Version in Chinese (Year: 2021).*
Google Patent Translation (English language) of WO 2018174226A1. (Year: 2018).*

* cited by examiner

COMPOUND CONTINUUM ROBOT FOR SKULL BASE TUMOR RESECTION AND CONTROL METHOD THEREFOR

TECHNICAL FIELD

The present disclosure belongs to the technical field of minimally invasive surgery robots, and more particularly relates to a compound continuum robot for skull base tumor resection and a control method therefor.

BACKGROUND

The application of a robotics technology in the field of minimally invasive surgery, such as in skull base tumor resection surgery, greatly increases safety and reliability of the surgery, makes operation of surgical instruments more flexible, and most importantly, solves the problem about fatigue of doctors during long-time surgery.

The inventors find that in existing robots for skull base tumor resection, various mechanisms have poor connection compactness in position, an overall drive function is incomplete, and the overall size of the robot is large, which influence application and popularization of the robots in the minimally invasive surgery.

SUMMARY

In order to solve the above problems, the present disclosure provides a compound continuum robot for skull base tumor resection and a control method therefor. A continuum mechanism is sequentially composed of a concentric tube continuum mechanism and a notched continuum mechanism from interior to exterior. Feeding and rotating motions of the notched continuum mechanism and feeding and rotating motions of the concentric tube continuum mechanism are respectively controlled by a notched continuum control mechanism and a concentric tube driving mechanism, and by adopting a compound driving manner, the continuum mechanism can adapt to a complex in vivo environment, performs surgical operations deep into the focus, and meanwhile reduces the diameter of surgical instruments.

In order to achieve the above objectives, in a first aspect, the present disclosure provides a compound continuum robot for skull base tumor resection and adopts a following technical solution:

Provided is a compound continuum robot for skull base tumor resection, including a fixed base module, and a continuum mechanism, a notched continuum control mechanism, a concentric tube driving mechanism and a forceps opening and closing control mechanism which are arranged on the fixed base module;

the continuum mechanism including a notched continuum mechanism and a concentric tube continuum mechanism located in the notched continuum mechanism; a tube being arranged in the concentric tube continuum mechanism and internally provided with a forceps opening and closing control mechanism steel cable;

the notched control mechanism being connected to the notched continuum mechanism; the concentric tube driving mechanism being connected to the concentric tube continuum mechanism; and the forceps opening and closing control mechanism being connected to the forceps opening and closing control mechanism steel cable.

Further, a plurality of steel cable holes are equally distributed in a circumferential direction of a tube wall of the notched continuum mechanism in array, and each steel cable hole is internally provided with a steel cable.

Further, the notched continuum control mechanism includes a guide rail holder, and a tail end of the notched continuum mechanism is fixedly connected to the guide rail holder; two ends of the guide rail holder are respectively connected, through bearings, to a first support and a second support on the fixed base module; the second support is provided with a power unit for driving the notched continuum control mechanism to rotate;

the guide rail holder is provided with a connector through a guide rail and a sliding block, and a tension sensor is fixed to the connector; a motor fixing block is fixed to the first support, a notched continuum mechanism lead screw is fixed to an output shaft of the motor fixing block, and the notched continuum control mechanism lead screw is connected to the connector through a notched continuum control mechanism screw nut.

Further, one end of the steel cable penetrates through the steel cable hole and is then fixed to the notched continuum mechanism, and the other end is fixed to the tension sensor.

Further, the concentric tube driving mechanism includes a concentric tube linear motion control mechanism lead screw supporting seat, a concentric tube linear motion control mechanism controller, a concentric tube linear motion control mechanism screw nut, a concentric tube linear motion control mechanism lead screw, a concentric tube linear motion control mechanism coupler, a concentric tube linear motion control mechanism motor base and a concentric tube linear motion control mechanism motor;

the concentric tube linear motion control mechanism motor is fixedly connected to the concentric tube linear motion control mechanism motor base, and the concentric tube linear motion control mechanism motor base is fixedly connected to a fifth support on the fixed base module; one end of the concentric tube linear motion control mechanism lead screw is in interference fit with a bearing in the concentric tube linear motion control mechanism lead screw supporting seat, and the other end is connected to the linear motion control motor through the coupler; the concentric tube linear motion control mechanism lead screw supporting seat is fixedly connected to a third support on the fixed base module; and one end of the concentric tube linear motion control mechanism controller is movably connected to the concentric tube linear motion control mechanism lead screw through the concentric tube linear motion control mechanism screw nut, and the other end is connected to the concentric tube continuum mechanism through a bearing.

Further, the concentric tube driving mechanism includes a concentric tube rotation control mechanism synchronous pulley, a first concentric tube rotation control mechanism synchronous pulley, a second concentric tube rotation control mechanism synchronous pulley and a concentric tube rotation control mechanism motor; the concentric tube rotation control mechanism motor is fixedly connected to a motor base; the motor base is fixedly connected to a fourth support on the fixed base module; the concentric tube continuum mechanism is fixedly connected to the second concentric tube rotation control mechanism synchronous pulley; the first concentric tube rotation control mechanism synchronous pulley is fixedly connected to an output shaft of the concentric tube rotation control mechanism motor; and the second concentric tube rotation control mechanism synchronous pulley is connected to the first concentric tube rotation control mechanism synchronous pulley through a belt.

Further, the concentric tube rotation control mechanism further includes a concentric tube rotation control mechanism synchronous belt tensioning adjusting bearing and a concentric tube rotation control mechanism synchronous belt tensioning adjusting bolt; the concentric tube rotation control mechanism synchronous belt tensioning adjusting bolt is movably connected to the concentric tube rotation control mechanism synchronous belt tensioning adjusting bearing.

Further, the forceps opening and closing control mechanism includes a forceps opening and closing control mechanism lead screw supporting seat, a forceps opening and closing control mechanism screw nut, a forceps opening and closing control mechanism lead screw, a forceps opening and closing control mechanism coupler, a forceps opening and closing control mechanism motor base, a forceps opening and closing control mechanism motor, the forceps opening and closing control mechanism steel cable, the tube and a second controller;

the forceps opening and closing control mechanism motor is fixedly connected to the forceps opening and closing control mechanism motor base, and the forceps opening and closing control mechanism motor base is fixedly connected to the fourth support on the fixed base module; one end of the forceps opening and closing control mechanism lead screw is in interference fit with a bearing in the forceps opening and closing control mechanism lead screw supporting seat, and the other end is connected to the forceps opening and closing control mechanism motor through the coupler; the forceps opening and closing control mechanism lead screw supporting seat is fixedly connected to a sixth support on the fixed base module; and one end of the second controller is movably connected to the forceps opening and closing control mechanism lead screw through the forceps opening and closing control mechanism screw nut, and the other end is connected to the forceps opening and closing control mechanism steel cable through a bearing.

Further, a forceps rotation control mechanism includes a forceps rotation control mechanism motor, a forceps rotation control mechanism synchronous belt tensioning adjusting bolt, a forceps rotation control mechanism synchronous belt tensioning adjusting bearing, a first forceps rotation control mechanism synchronous pulley and a second forceps rotation control mechanism synchronous pulley;

the forceps rotation control mechanism motor is fixedly connected to a motor base, and the motor base is fixedly connected to the fifth support on the fixed base module; the forceps opening and closing control mechanism steel cable is fixedly connected to the second forceps rotation control mechanism synchronous pulley; the first forceps rotation control mechanism synchronous pulley is fixedly connected to an output shaft of the forceps rotation control mechanism motor; and the first forceps rotation control mechanism synchronous pulley and the second forceps rotation control mechanism synchronous pulley are connected through a belt.

In order to achieve the above objectives, in a second aspect, the present disclosure further provides a method for controlling a compound continuum robot for skull base tumor resection and adopts a following technical solution:

The method for controlling the compound continuum robot for skull base tumor resection adopts the compound continuum robot for skull base tumor resection in the first aspect, and includes: controlling a bending motion and a rotating motion of the notched continuum mechanism by the notched continuum control mechanism, controlling feeding and rotating motions of the concentric tube continuum mechanism by the concentric tube driving mechanism, and controlling feeding and rotating motions of the forceps opening and closing control mechanism steel cable by the forceps opening and closing control mechanism, such that forceps are opened or closed.

The notched continuum mechanism completely coincides with the concentric tube continuum mechanism. The rotating motion of the concentric tube continuum mechanism is controlled by the concentric tube driving mechanism, such that a pre-bending direction of the concentric tube continuum mechanism is opposite to a load direction all the time so as to enhance stiffness of the robot, and the bending motion and the rotating motion of the notched continuum mechanism are controlled by the notched continuum driving mechanism and the notched continuum control mechanism so as to achieve a motion of a tail end of the continuum mechanism. The bending motion and the rotating motion of the notched continuum mechanism are controlled by the notched continuum control mechanism, the feeding and rotating motions of the concentric tube continuum mechanism are controlled by the concentric tube driving mechanism, and the motion of the tail end of the continuum mechanism is achieved under the cooperation of the notched continuum driving mechanism and the concentric tube driving mechanism, such that a robotic arm can operate with high dexterity. A feeding motion range of the concentric tube continuum mechanism is controlled inside the notched continuum mechanism, the feeding and rotating motions of the concentric tube continuum mechanism are controlled by the concentric tube driving mechanism, such that the shape of the notched continuum mechanism is changed due to a coupling effect of the concentric tube continuum mechanism on the notched continuum mechanism, the bending motion and the rotating motion of the notched continuum mechanism are controlled by the notched continuum control mechanism, such that a pre-bending angle of the concentric tube continuum mechanism is changed due to a coupling effect of the notched continuum mechanism on the concentric tube continuum mechanism, and by utilizing mutual coupling of the notched continuum mechanism and the concentric tube continuum mechanism, the high-precision motion of the tail end of the continuum mechanism is realized.

Compared with the prior art, the present disclosure has the following beneficial effects:

1. The continuum mechanism in the present disclosure is sequentially composed of the concentric tube continuum mechanism and the notched continuum mechanism from interior to exterior; the bending motion and the rotating motion of the notched continuum mechanism are controlled by the notched continuum control mechanism, the feeding and rotating motions of the concentric tube continuum mechanism are controlled by the concentric tube driving mechanism, and the feeding and rotating motions of the forceps opening and closing control mechanism steel cable are controlled by the forceps opening and closing control mechanism, such that forceps are opened or closed; and by adopting a compound driving manner, the continuum mechanism can adapt to a complex in vivo environment, performs surgical operations deep into the focus, is compact in overall structure and reduces the diameter of surgical instruments.

2. A deflection control mechanism in the present disclosure realizes a spatial motion of the notched continuum mechanism through four steel cables, such that stiffness of the continuum is higher, and surgical environment adaptability is better.
3. The continuum mechanism in the present disclosure is sequentially composed of the concentric tube continuum mechanism and the notched continuum mechanism from interior to exterior, and when the concentric tube continuum mechanism completely coincides with the notched continuum mechanism, the continuum can obtain high stiffness, and surgical environment adaptability is better.
4. The continuum mechanism in the present disclosure is controlled by the notched continuum control mechanism and the concentric tube driving mechanism, the continuum mechanism can obtain high dexterity under cooperation of the two driving mechanisms so as to adapt to the complex in vivo environment, perform surgical operations deep into the focus, and be compact in overall structure and high in space utilization rate.
5. The continuum mechanism in the present disclosure is composed of the concentric tube continuum mechanism and the notched continuum mechanism, which are coupled, and when the feeding motion range of the concentric tube continuum mechanism is controlled inside the notched continuum mechanism, the coupling can be utilized for finishing precise operation of the continuum mechanism.

BRIEF DESCRIPTION OF THE DRAWINGS

The accompanying drawings of the specification constituting a part of this embodiment are used to provide a further understanding of this embodiment. The exemplary embodiments of this embodiment and descriptions thereof are used to explain this embodiment, but do not constitute an improper limitation to this embodiment.

Figure 1:
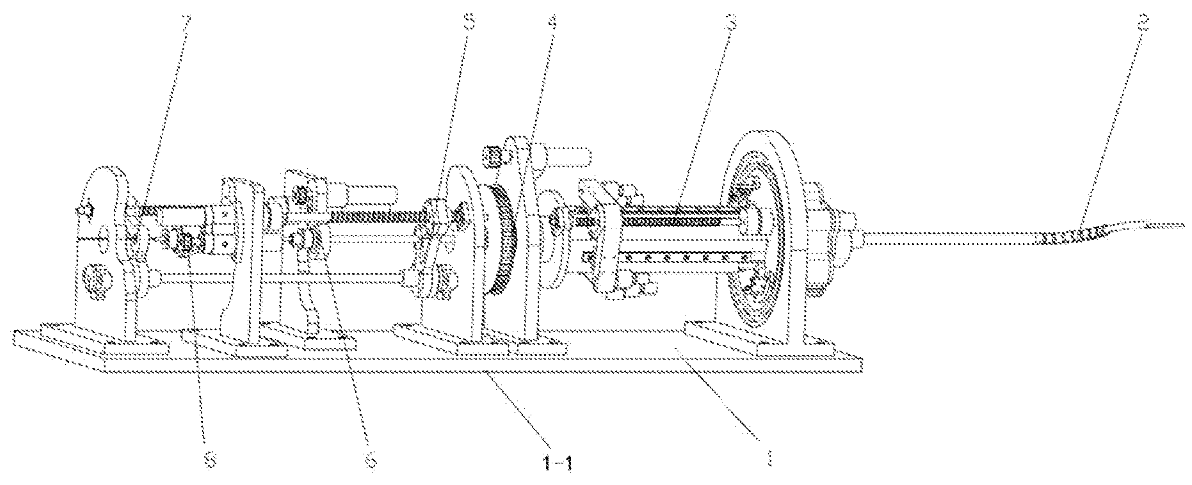
FIG. 1 is a schematic diagram of overall structure according to Embodiment 1 of the present disclosure.

In the drawings: 1: fixed base module; 1-1: base; 1-2: first support; 1-3: second support; 1-4: third support; 1-5: fourth support; 1-6: fifth support; 1-7: sixth support; 2: continuum mechanism; 2-1: notched continuum mechanism; 2-2: concentric tube continuum mechanism; 3: notched continuum control mechanism; 3-1: notched continuum control mechanism motor module; 3-1-1: notched continuum control mechanism motor; 3-1-2: first guide wheel; 3-1-3: second guide wheel; 3-1-4: motor fixing block; 3-2: third guide wheel; 3-3: guide wheel frame; 3-4: notched continuum control mechanism coupler; 3-5: guide wheel; 3-6: notched continuum control mechanism lead screw; 3-7: notched continuum control mechanism lead screw supporting seat; 3-8: connector; 3-9: notched continuum control mechanism screw nut; 3-10: sliding block; 3-11: guide rail holder; 3-12: tension sensor; 4: notched continuum driving mechanism; 4-1: first notched continuum driving mechanism radial ball bearing; 4-2: notched continuum driving mechanism motor; 4-3: notched continuum driving mechanism synchronous pulley; 4-3-1: first notched continuum driving mechanism synchronous pulley; 4-3-2: second notched continuum driving mechanism synchronous pulley; 4-4: second notched continuum driving mechanism radial ball bearing; 5: concentric tube linear motion control mechanism; 5-1: concentric tube linear motion control mechanism lead screw supporting seat; 5-2: first controller; 5-3: concentric tube linear motion control mechanism screw nut; 5-4: concentric tube linear motion control mechanism lead screw; 5-5: concentric tube linear motion control mechanism coupler; 5-6: polish rod; 5-7: concentric tube linear motion control mechanism motor base; 5-8: concentric tube linear motion control mechanism motor; 5-9: first polish rod fixing base; 5-10: second polish rod fixing base; 6: concentric tube rotation control mechanism; 6-1: concentric tube rotation control mechanism synchronous pulley; 6-1-1: first concentric tube rotation control mechanism synchronous pulley; 6-1-2: second concentric tube rotation control mechanism synchronous pulley; 6-2: concentric tube rotation control mechanism synchronous belt tensioning adjusting bearing; 6-3: concentric tube rotation control mechanism synchronous belt tensioning adjusting bolt; 6-4: concentric tube rotation control mechanism motor; 7: forceps opening and closing control mechanism; 7-1: forceps opening and closing control mechanism lead screw supporting seat; 7-2: forceps opening and closing control mechanism screw nut; 7-3: forceps opening and closing control mechanism lead screw; 7-4: forceps opening and closing control mechanism coupler; 7-5: forceps opening and closing control mechanism motor base; 7-6: forceps opening and closing control mechanism motor; 7-7: forceps opening and closing control mechanism steel cable; 7-8: tube; 7-9: second controller; 8: forceps rotation control mechanism; 8-1: forceps rotation control mechanism motor; 8-2: forceps rotation control mechanism synchronous belt tensioning adjusting bolt; 8-3: forceps rotation control mechanism synchronous belt tensioning adjusting bearing; 8-4: forceps rotation control mechanism synchronous pulley; 8-4-1: first forceps rotation control mechanism synchronous pulley; and 8-4-2: second forceps rotation control mechanism synchronous pulley.

DETAILED DESCRIPTION

The present disclosure is further described below by combining the accompanying drawings and the embodiments.

It should be noted that the following detailed descriptions are all illustrative and are intended to further describe the present disclosure. Unless otherwise specified, all technological and scientific terms used in the present disclosure have the same meaning as usually understood by those of ordinary skill in the art of this application.

Embodiment 1

As shown in FIG. 1, this embodiment provides a compound continuum robot for skull base tumor resection, including a fixed base module 1, and a continuum mechanism 2, a notched continuum control mechanism 3, a notched continuum driving mechanism 4, a concentric tube linear motion control mechanism 5, a concentric tube rotation control mechanism 6, a forceps opening and closing control mechanism 7, a forceps rotation control mechanism 8, and the like which are arranged on the fixed base module 1.

As shown in FIG. 1, FIG. 2, FIG. 5, FIG. 6, FIG. 7 and FIG. 8, the fixed base module 1 includes a base 1-1, a first support 1-2, a second support 1-3, a third support 1-4, a fourth support 1-5, a fifth support 1-6 and a sixth support 1-7. The first support 1-2, the second support 1-3, the third support 1-4, the fourth support 1-5, the fifth support 1-6 and the sixth support 1-7 are all fixedly connected to the base 1-1, and specifically, are fixedly connected through bolts, welding or the like.

As shown in FIG. 1, FIG. 2, FIG. 4 and FIG. 5, the continuum mechanism 2 includes a notched continuum mechanism 2-1 and a concentric tube continuum mechanism 2-2. A tail end of the notched continuum mechanism 2-1 is fixedly connected to a guide rail holder 3-11. A plurality of steel cable holes are equally distributed in a circumference of a tube wall of the notched continuum mechanism 2-1 in array, and each steel cable hole is internally provided with a steel cable. In this embodiment, there may be four steel cable holes, and four deflection control steel cables are correspondingly arranged in the four steel cable holes equally distributed in the circumference of the tube wall of the notched continuum mechanism 2-1 in array. When the deflection control steel cables respectively stretch and contract, the notched continuum mechanism 2-1 is driven to perform 360-degree deflection and pitching motions in space.

Figure 2:
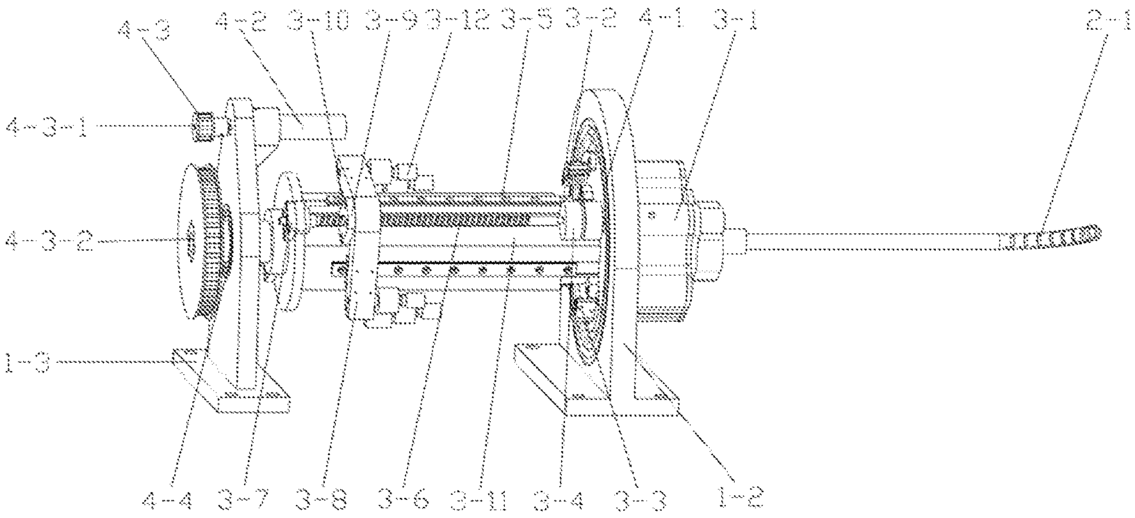
FIG. 2 is a schematic structural diagram of a notched continuum mechanism, and a notched continuum control mechanism and a notched continuum driving mechanism arranged on a fixed base module according to Embodiment 1 of the present disclosure.
Figure 3:
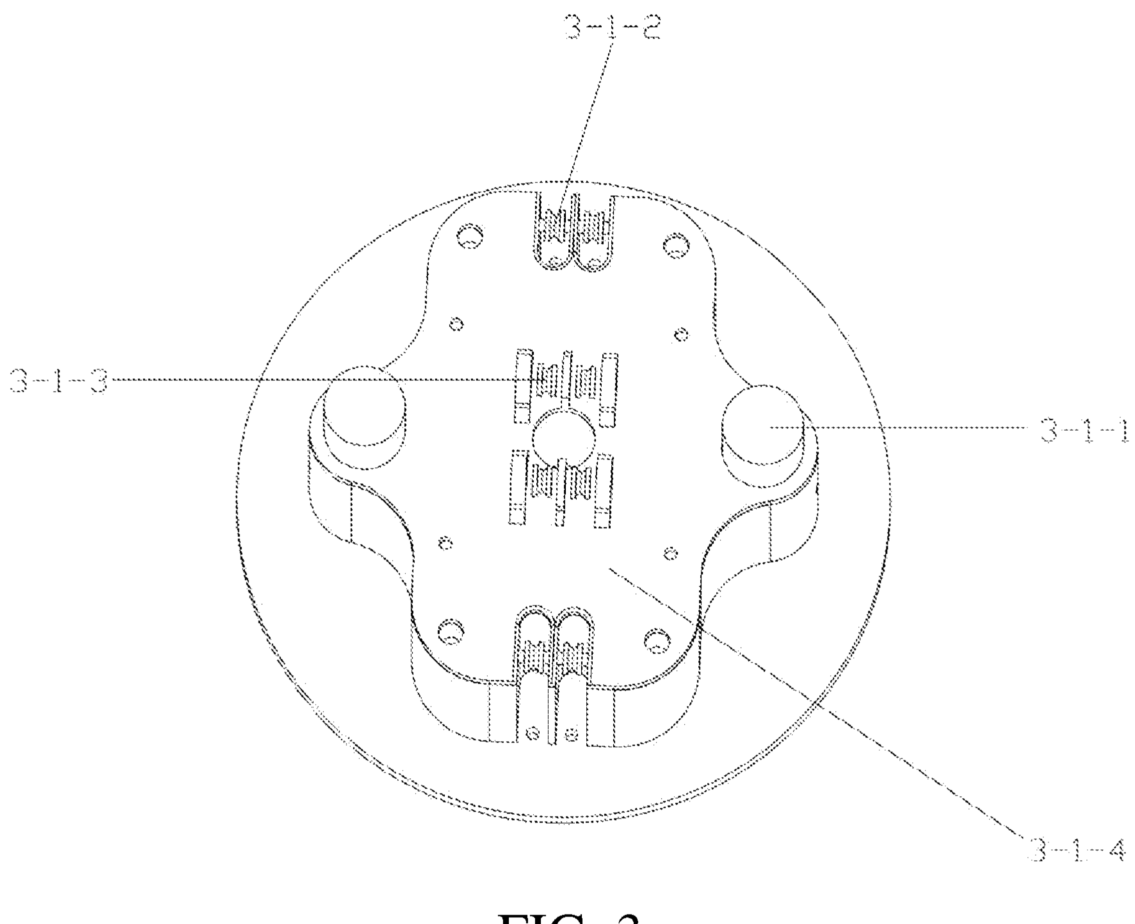
FIG. 3 is a schematic structural diagram of a notched continuum control mechanism motor module according to Embodiment 1 of the present disclosure.
Figure 4:
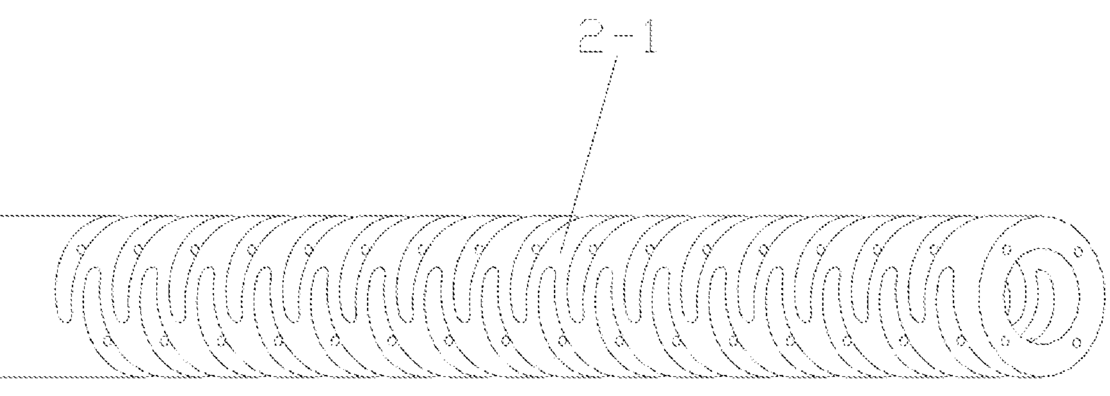
FIG. 4 is a schematic structural diagram of a notched continuum mechanism according to Embodiment 1 of the present disclosure.

The notched continuum control mechanism 3 includes the guide rail holder 3-11, and the tail end of the notched continuum mechanism 2-1 is fixedly connected to the guide rail holder 3-11. Two ends of the guide rail holder 3-11 are respectively connected, through bearings, to the first support 1-2 and the second support 1-3 on the fixed base module. The second support 1-3 is provided with a power unit for driving the notched continuum control mechanism 3 to rotate. The guide rail holder 3-11 is provided with a connector 3-8 through a guide rail 3-5 and a sliding block 3-10, and a tension sensor 3-12 is fixed to the connector 3-8. A motor fixing block 3-1-4 is fixed to the first support 1-2, a notched continuum control mechanism lead screw 3-6 is fixed to an output shaft of the motor fixing block 3-1-4, and the notched continuum control mechanism lead screw 3-6 is connected to the connector 3-8 through a notched continuum control mechanism screw nut 3-9. Specifically, as shown in FIG. 2, FIG. 3 and FIG. 4, the notched continuum control mechanism 3 includes a notched continuum control mechanism motor module 3-1, a notched continuum control mechanism motor 3-1-1, a first guide wheel 3-1-2, a second guide wheel 3-1-3, the motor fixing block 3-1-4, a third guide wheel 3-2, a guide wheel frame 3-3, a notched continuum control mechanism coupler 3-4, the guide rail 3-5, the notched continuum control mechanism lead screw 3-6, a notched continuum control mechanism lead screw supporting seat 3-7, the connector 3-8, the notched continuum control mechanism screw nut 3-9, the sliding block 3-10, the guide rail holder 3-11, the tension sensors 3-12, etc. Specifically, there are two sets of components of the notched continuum control mechanism 3 forming a circumferential equal-array structure in the space, but only one set of components is explained herein. To clearly describe the relationship among the components, as shown in FIG. 3, components unrelated to the part of description are dismounted, the notched continuum control mechanism motor 3-1-1 is fixedly connected to the motor fixing block 3-1-4, and the motor fixing block 3-1-4 is fixedly connected to the first support 1-2. The third guide wheel 3-2 is arranged on the guide wheel frame 3-3, the guide wheel frame 3-3 is fixedly connected to the first support 1-2, and the first guide wheel 3-1-2 and the second guide wheel 3-1-3 are arranged on the motor fixing block 3-1-4. One end of the notched continuum control mechanism lead screw 3-6 is connected to the notched continuum control mechanism motor 3-1-1 through the notched continuum control mechanism coupler 3-4, and the other end is in interference fit with a bearing in the notched continuum control mechanism lead screw supporting seat 3-7. The other end of the notched continuum control mechanism lead screw supporting seat 3-7 is fixedly connected to the guide rail holder 3-11. One end of the notched continuum control mechanism screw nut 3-9 and the notched continuum control mechanism lead screw 3-6 are movably connected after being in threaded fit, and the other end is fixedly connected to the connector 3-8. The other end of the connector 3-8 is fixedly connected to the sliding block 3-10. The sliding block 3-10 is movably connected to the guide rail holder 3-11 through the guide rail 3-5. One end of the guide rail holder 3-11 is movably connected to the first support 1-2 through a first notched continuum driving mechanism radial ball bearing 4-1, and the other end of is movably connected to the second support 1-3 through a second notched continuum driving mechanism radial ball bearing 4-4. The tension sensor 3-12 is fixedly connected to the notched continuum control mechanism screw nut 3-9 through the connector 3-8. One end of the deflection control steel cable is fixedly connected to the tension sensor 3-12 and is diverted through the third guide wheel 3-2, the first guide wheel 3-1-2 and the second guide wheel 3-1-3, and the other end is fixedly connected to a port of the notched continuum mechanism 2-1 through the four cable holes arranged in the notched continuum mechanism 2-1 in a circumferential equal-array structure. When the notched continuum control mechanism motor 3-1-1 rotates, the notched continuum control mechanism lead screw 3-6 is driven to rotate, such that the notched continuum control mechanism screw nut 3-9 drives, through the connector 3-8, the tension sensor 3-12 to do a forward or backward linear motion, so as to drive the deflection control steel cable to do a stretching and contracting motion, and the deflection control steel cable adjusts a space deflection condition of the notched continuum mechanism 2-1. The other set of components of the notched continuum control mechanism 3 is of a circumferential equal-array structure in the space, and the specific arrangement and working principle will not be described in detail herein.

As shown in FIG. 2, the notched continuum driving mechanism 4 includes the first notched continuum driving mechanism radial ball bearing 4-1, a notched continuum driving mechanism motor 4-2, a first notched continuum driving mechanism synchronous pulley 4-3-1, a second notched continuum driving mechanism synchronous pulley 4-3-2, a notched continuum driving mechanism synchronous pulley 4-3, the second notched continuum driving mechanism radial ball bearing 4-4, and the like. According to the working principle of the notched continuum driving mechanism 4, the notched continuum driving mechanism motor 4-2 is fixedly connected to the second support 1-3; and one end of the first notched continuum driving mechanism synchronous pulley 4-3-1 is fixedly connected to an output shaft of the notched continuum driving mechanism motor 4-2, and the other end is connected to the second notched continuum driving mechanism synchronous pulley 4-3-2 through synchronous belt transmission. When the notched continuum driving mechanism motor 4-2 rotates, the first notched continuum driving mechanism synchronous pulley 4-3-1 is driven to rotate, the second notched continuum driving mechanism synchronous pulley 4-3-2 rotates through synchronous belt transmission, and then the notched continuum mechanism 2-1 is driven to rotate through the guide rail holder 3-11.

Figure 5:
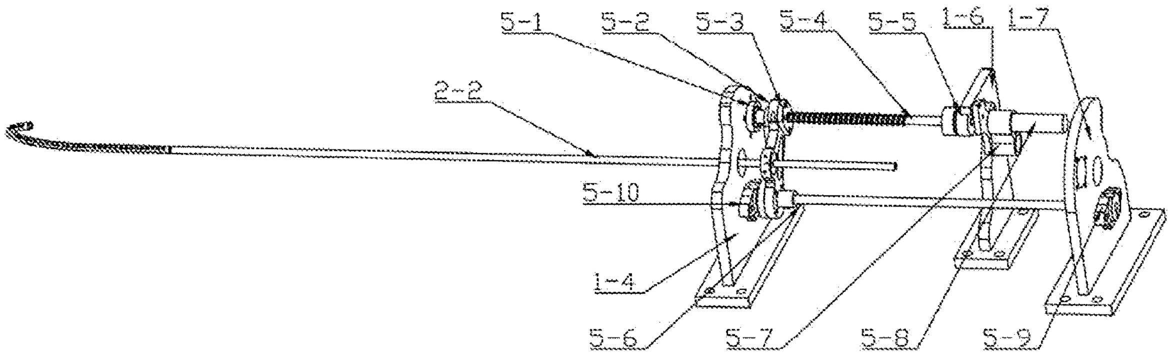
FIG. 5 is a schematic structural diagram of a concentric tube linear motion control mechanism according to Embodiment 1 of the present disclosure.

As shown in FIG. 5, the concentric tube linear motion control mechanism 5 includes a concentric tube linear motion control mechanism lead screw supporting seat 5-1, a first controller 5-2, a concentric tube linear motion control mechanism screw nut 5-3, a concentric tube linear motion control mechanism lead screw 5-4, a concentric tube linear motion control mechanism coupler 5-5, a polish rod 5-6, a concentric tube linear motion control mechanism motor base 5-7, a concentric tube linear motion control mechanism motor 5-8, a first polish rod fixing base 5-9, a second polish rod fixing base 5-10, and the like. According to the working principle of the concentric tube linear motion control mechanism 5, the linear motion control motor 5-8 is fixedly connected to the motor base 5-7, and the motor base 5-7 is fixedly connected to the fifth support 1-6. One end of the lead screw 5-4 is in interference fit with a bearing in the lead screw supporting seat 5-1, and the other end is connected to the linear motion control motor 5-8 through the coupler 5-5. The lead screw supporting seat 5-1 is fixedly connected to the third support 1-4. One end of the first controller 5-2 is movably connected to the lead screw 5-4 through the concentric tube linear motion control mechanism screw nut 5-3, and the other end of the first is connected to the concentric tube continuum mechanism 2-2 through a bearing, is also movably connected to the polish rod 5-6 through a bearing, and may also be movably connected to the polish rod 5-6 through a linear bearing. The polish rod 5-6 is connected to the sixth support 1-7 through the first polish rod fixing base 5-9 and is fixedly connected to the sixth support 1-7 through the second polish rod fixing base 5-10. When the linear motion control motor 5-8 rotates, the lead screw 5-4 is driven to rotate, and the first controller 5-2 drives the concentric tube continuum mechanism 2-2 to do a forward or backward linear feeding motion. The first controller 5-2 and the polish rod 5-6 are connected to ensure a horizontal motion of the concentric tube continuum mechanism 2-2.

Figure 6:
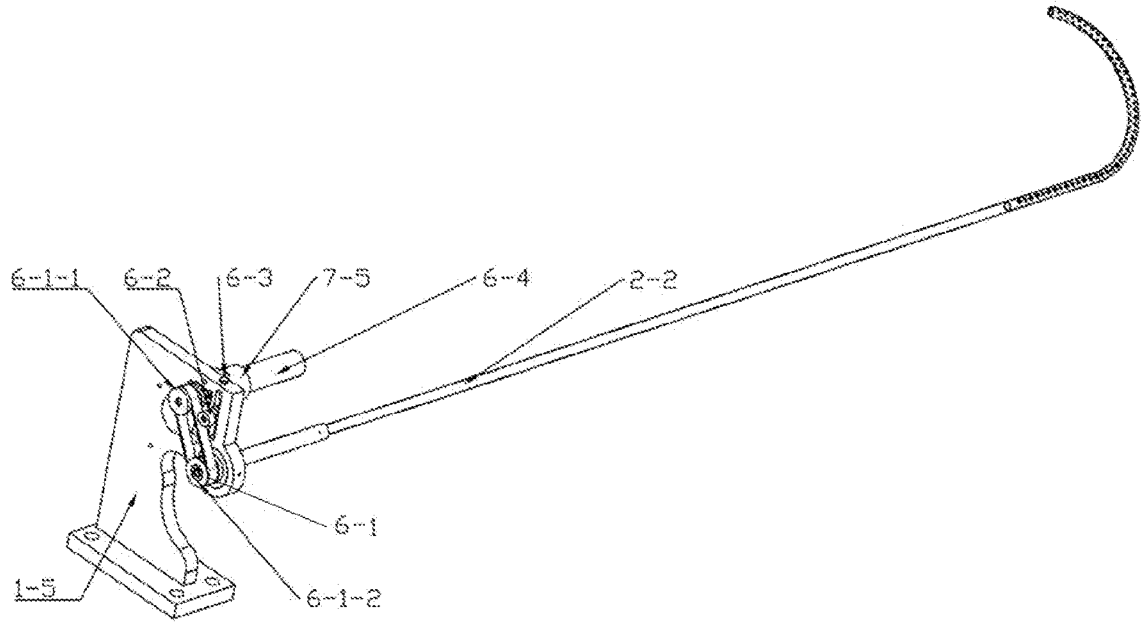
FIG. 6 is a schematic structural diagram of a concentric tube rotation control mechanism according to Embodiment 1 of the present disclosure.

As shown in FIG. 6, the concentric tube rotation control mechanism 6 includes a concentric tube rotation control mechanism synchronous pulley 6-1, a first concentric tube rotation control mechanism synchronous pulley 6-1-1, a second concentric tube rotation control mechanism synchronous pulley 6-1-2, a concentric tube rotation control mechanism synchronous belt tensioning adjusting bearing 6-2, a concentric tube rotation control mechanism synchronous belt tensioning adjusting bolt 6-3, a concentric tube rotation control mechanism motor 6-4, and the like. According to the working principle of the concentric tube rotation control mechanism 6, the concentric tube rotation control mechanism motor 6-4 is fixedly connected to the motor base 5-7; the motor base 5-7 is fixedly connected to the fourth support 1-5. The concentric tube continuum mechanism 2-2 is fixedly connected to the second concentric tube rotation control mechanism synchronous pulley 6-1-2. The first concentric tube rotation control mechanism synchronous pulley 6-1-1 is fixedly connected to an output shaft of the concentric tube rotation control mechanism motor 6-4. The second concentric tube rotation control mechanism synchronous pulley 6-1-2 is connected to the first concentric tube rotation control mechanism synchronous pulley 6-1-1 through a belt. In this embodiment, the concentric tube rotation control mechanism synchronous belt tensioning adjusting bolt 6-3 is movably connected to the concentric tube rotation control mechanism synchronous belt tensioning adjusting bearing 6-2. In other embodiments, the concentric tube rotation control mechanism synchronous belt tensioning adjusting bolt 6-3 and the concentric tube rotation control mechanism synchronous belt tensioning adjusting bearing 6-2 may not be arranged, and at this time, the belt is unadjustable in tension. When the concentric tube rotation control mechanism motor 6-4 rotates, the first concentric tube rotation control mechanism synchronous pulley 6-1-1 is driven to rotate, and the first concentric tube rotation control mechanism synchronous pulley 6-1-1 drives, by the belt, the second concentric tube rotation control mechanism synchronous pulley 6-1-2 to rotate, and then the concentric tube continuum mechanism 2-2 is driven to rotate. When the concentric tube rotation control mechanism synchronous belt tensioning adjusting bolt 6-3 is rotated, the concentric tube rotation control mechanism synchronous belt tensioning adjusting bearing 6-2 is driven to rotate up and down, and then the belt is adjusted to be tensioned.

Figure 7:
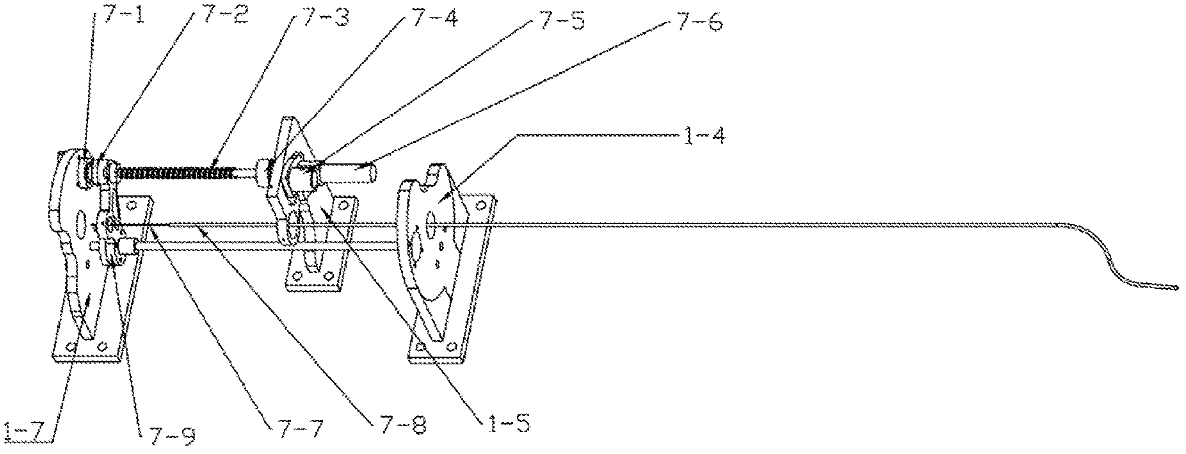
FIG. 7 is a schematic structural diagram of a forceps opening and closing control mechanism according to Embodiment 1 of the present disclosure.

As shown in FIG. 7, the forceps opening and closing control mechanism 7 includes a forceps opening and closing control mechanism lead screw supporting seat 7-1, a forceps opening and closing control mechanism screw nut 7-2, a forceps opening and closing control mechanism lead screw 7-3, a forceps opening and closing control mechanism coupler 7-4, a forceps opening and closing control mechanism motor base 7-5, a forceps opening and closing control mechanism motor 7-6, a forceps opening and closing control mechanism steel cable 7-7, a tube 7-8, a second controller 7-9, and the like. According to the working principle of the forceps opening and closing control mechanism 7, the forceps opening and closing control mechanism motor 7-6 is fixedly connected to the motor base 7-5, and the motor base 7-5 is fixedly connected to the fourth support 1-5. One end of the lead screw 7-3 is in interference fit with a bearing in the lead screw supporting seat 7-1, and the other end is connected to the forceps opening and closing control mechanism motor 7-6 through the coupler 7-4. The lead screw supporting seat 7-1 is fixedly connected to the sixth support 1-7. One end of the second controller 7-9 is movably connected to the lead screw 7-3 through the screw nut 7-2, and the other end is connected to the forceps opening and closing control mechanism steel cable 7-7 through a bearing, is also movably connected to the polish rod 5-6 through a bearing, and may also be movably connected to the polish rod 5-6 through a linear bearing. When the forceps opening and closing motor 7-6 is controlled to rotate, the lead screw 7-3 is driven to rotate, such that the second controller 7-9 drives the forceps opening and closing control mechanism steel cable 7-7 to do a forward or backward motion, and accordingly, forceps are controlled to be opened or closed. The second controller 7-9 is connected to the polish rod so as to ensure a horizontal motion of the forceps opening and closing control mechanism steel cable.

Figure 8:
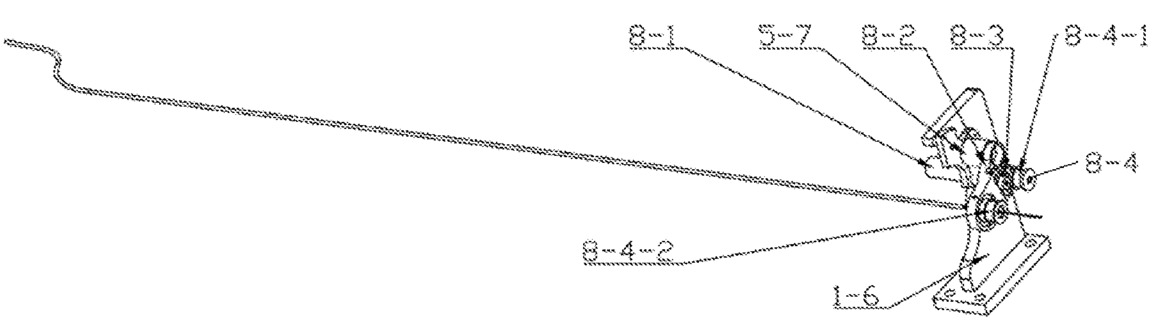
FIG. 8 is a schematic structural diagram of a forceps rotation control mechanism according to Embodiment 1 of the present disclosure.

As shown in FIG. 8, the forceps rotation control mechanism 8 includes a forceps rotation control mechanism motor 8-1, a forceps rotation control mechanism synchronous belt tensioning adjusting bolt 8-2, a forceps rotation control mechanism synchronous belt tensioning adjusting bearing 8-3, a first forceps rotation control mechanism synchronous pulley 8-4-1 and a second forceps rotation control mechanism synchronous pulley 8-4-2. According to the working principle of the forceps rotation control mechanism 8, the forceps rotation control mechanism motor 8-1 is fixedly connected to the motor base 5-7, and the motor base 5-7 is fixedly connected to the fifth support 1-6. The forceps opening and closing control mechanism steel cable 7-7 is fixedly connected to the second forceps rotation control mechanism synchronous pulley 8-4-2. The first forceps rotation control mechanism synchronous pulley 8-4-1 is fixedly connected to an output shaft of the forceps rotation control mechanism motor 8-1. Two pulleys are connected through a belt. The forceps rotation control mechanism synchronous belt tensioning adjusting bolt 8-2 is movably connected to the forceps rotation control mechanism synchronous belt tensioning adjusting bearing 8-3. When the forceps rotation control mechanism 8-1 rotates, the first forceps rotation control mechanism synchronous pulley 8-4-1 is driven to rotate, the first forceps rotation control mechanism synchronous pulley 8-4-1 drives, by a belt, the second forceps rotation control mechanism synchronous pulley 8-4-2 to rotate, and then the forceps opening and closing control mechanism steel cable 7-7 is driven to rotate. In this embodiment, when the forceps rotation control mechanism synchronous belt tensioning adjusting bolt 8-2 is adjusted, the forceps rotation control mechanism synchronous belt tensioning adjusting bearing 8-3 is driven to move up and down, so as to adjust belt tension. In other embodiments, the forceps rotation control mechanism synchronous belt tensioning adjusting bolt 8-2 and the forceps rotation control mechanism synchronous belt tensioning adjusting bearing 8-3 may not be arranged, and at this time, the belt tension cannot be adjusted.

In this embodiment, the concentric tube continuum mechanism 2-2 is located in the notched continuum mechanism 2-1 and penetrates through the notched continuum mechanism 2-1, and the tube 7-8 is located in the concentric tube continuum mechanism 2-2 and penetrates through the concentric tube continuum mechanism 2-2, which both belong to conventional arrangements. The forceps opening and closing control mechanism steel cable 7-7 penetrates through the tube 7-8 and is connected to the forceps to control the forceps, which all belong to conventional arrangements, and further detailed descriptions are omitted here.

Embodiment 2

This embodiment provides a method for controlling a compound continuum robot for skull base tumor resection, using the compound continuum robot for skull base tumor resection according to Embodiment 1. The control method includes: a bending motion and a rotating motion of the notched continuum mechanism 2-1 are controlled by the notched continuum control mechanism 3, feeding and rotating motions of the concentric tube continuum mechanism 2-2 are controlled by a concentric tube driving mechanism, and feeding and rotating motions of the forceps opening and closing control mechanism steel cable 7-7 are controlled by the forceps opening and closing control mechanism 7, such that forceps are opened or closed.

The above embodiments are merely preferred embodiments of this embodiment, and are not used for limiting this embodiment, and this embodiment may be variously modified and changed by those skilled in the art. Any modification, equivalent substitution, improvement, and the like made within the spirit and principle of this embodiment shall fall within the scope of protection of this embodiment.

What is claimed is:

1. A compound continuum robot for skull base tumor resection, comprising:

a fixed base module, and a continuum mechanism, a notched continuum control mechanism, a notched continuum driving mechanism, a concentric tube driving mechanism and a forceps opening and closing control mechanism which are arranged in sequence on the fixed base module, wherein:

the continuum mechanism comprises a notched continuum mechanism and a concentric tube continuum mechanism located in-inside the notched continuum mechanism and penetrating through the notched continuum mechanism; a tube being arranged inside the concentric tube continuum mechanism and penetrating through the concentric tube continuum mechanism and internally provided with a forceps opening and closing control mechanism steel cable;

a first support, a second support, a third support, a fourth support, a fifth support, and a sixth support are fixed to a base of the fixed base module;

the notched continuum control mechanism is connected to the notched continuum mechanism; the concentric tube driving mechanism is connected to the concentric tube continuum mechanism; and the forceps opening and closing control mechanism is connected to the forceps opening and closing control mechanism steel cable;

the notched continuum control mechanism comprises a guide rail holder;

a tail end of the notched continuum mechanism is fixedly connected to the guide rail holder;

two ends of the guide rail holder are respectively connected to the first support and the second support through bearings;

a power unit is provided on the second support, and is configured to drive the notched continuum control mechanism to rotate;

the notched continuum driving mechanism comprises;

a first notched continuum driving mechanism radial ball bearing, a notched continuum driving mechanism motor, a first notched continuum driving mechanism pulley, a second notched continuum driving mechanism pulley, a notched continuum driving mechanism pulley, and a second notched continuum driving mechanism radial ball bearing:

the notched continuum driving mechanism motor is fixedly connected to the second support, the first notched continuum driving mechanism pulley is fixedly connected to an output shaft of the notched continuum driving mechanism motor, and the first notched continuum driving mechanism pulley is connected to the second notched continuum driving mechanism pulley;

the notched continuum driving mechanism motor is configured to rotate the first notched continuum driving mechanism pulley, thereby causing the second notched continuum driving mechanism pulley rotate, and to drive the notched continuum mechanism to rotate through the guide rail holder;

the concentric tube driving mechanism comprises:

a concentric tube linear motion control mechanism, and a concentric tube rotation control mechanism, the concentric tube linear motion control mechanism comprises:

a concentric tube linear motion control mechanism lead screw supporting seat, a first controller, a concentric tube linear motion control mechanism screw nut, a concentric tube linear motion control mechanism lead screw, a concentric tube linear motion control mechanism coupler, a concentric tube linear motion control mechanism motor base, a concentric tube linear motion control mechanism motor, and a polish rod, a first polish rod fixing base, and a second polish rod fixing base;

the concentric tube linear motion control mechanism lead screw supporting seat is fixedly connected to the third support;

the concentric tube linear motion control mechanism motor is fixedly connected to the concentric tube linear motion control mechanism motor base;

the concentric tube linear motion control mechanism motor base is fixedly connected to the fifth support;

a first end of the concentric tube linear motion control mechanism lead screw is in interference fit with a bearing in the concentric tube linear motion control mechanism lead screw supporting seat, and a second end of the concentric tube linear motion control mechanism lead screw is connected to the linear motion control motor through the concentric tube linear motion control mechanism coupler;

a first end of the first controller is movably connected to the concentric tube linear motion control mechanism lead screw through the concentric tube linear motion control mechanism screw out, and a second end of the first controller is connected to the concentric tube continuum mechanism and is movably connected to the polish rod through a bearing;

a first end of the polish rod is fixedly connected to the third support through the second polish rod fixing base, and a second end of the polish rod is connected to the sixth support through the first polish rod fixing base;

the concentric tube linear motion control mechanism motor is configured to rotate the concentric tube linear motion control mechanism lead screw, thereby driving the concentric tube continuum mechanism to perform a forward or backward linear feeding motion;

the first controller and the polish rod are configured to be connected to each other to define a horizontal motion of the concentric tube continuum mechanism;

the concentric tube driving mechanism comprises;

a concentric tube rotation control mechanism pulley, first concentric tube rotation control mechanism pulley, a second concentric tube rotation control mechanism pulley, and a concentric tube rotation control mechanism motor;

a forceps opening and closing control mechanism motor base is fixedly connected to the fourth support;

the concentric tube rotation control mechanism motor is fixedly connected to the forceps opening and closing control mechanism motor base;

the concentric tube continuum mechanism is fixedly connected to the second concentric tube rotation control mechanism pulley;

the first concentric tube rotation control mechanism pulley is fixedly connected to an output shaft of the concentric tube rotation control mechanism motor;

the second concentric tube rotation control mechanism pulley is connected to the first concentric tube rotation control mechanism pulley;

the concentric tube rotation control mechanism motor is configured to rotate the first concentric tube rotation control mechanism pulley, thereby driving the second concentric tube rotation control mechanism pulley to rotate, and to drive the concentric tube continuum mechanism to rotate.

2. The compound continuum robot for skull base tumor resection according to claim 1, wherein a plurality of steel cable holes are equally distributed in a circumferential direction of a tube wall of the notched continuum mechanism in array, and each of the plurality of steel cable holes is internally provided with a steel cable.

3. The compound continuum robot for skull base tumor resection according to claim 2, wherein the guide rail holder is provided with a connector through a guide rail and a sliding block, and a tension sensor is fixed to the connector, a motor fixing block is fixed to the first support, a notched continuum control mechanism lead screw is fixed to an output shaft of the motor fixing block, and the notched continuum control mechanism lead screw is connected to the connector through a notched continuum control mechanism screw nut.

4. The compound continuum robot for skull base tumor resection according to claim 3, wherein a first end of each steel cable penetrates through a corresponding one of the steel cable holes and is fixed to the notched continuum mechanism, and second end of each steel cable is fixed to the tension sensor.

5. The compound continuum robot for skull base tumor resection according to claim 1, wherein the concentric tube rotation control mechanism further comprises a concentric tube rotation control mechanism belt tensioning adjusting bearing and a concentric tube rotation control mechanism belt tensioning adjusting bolt; and the concentric tube rotation control mechanism belt tensioning adjusting bolt is movably connected to the concentric tube rotation control mechanism belt tensioning adjusting bearing.

6. The compound continuum robot for skull base tumor resection according to claim 1, wherein the forceps opening and closing control mechanism comprises a forceps opening and closing control mechanism lead screw supporting seat, a forceps opening and closing control mechanism screw nut, a forceps opening and closing control mechanism lead screw, a forceps opening and closing control mechanism coupler, the forceps opening and closing control mechanism motor base, a forceps opening and closing control mechanism motor, the forceps opening and closing control mechanism steel cable, the tube and a second controller;

the forceps opening and closing control mechanism motor is fixedly connected to the forceps opening and closing control mechanism motor base, and the forceps opening and closing control mechanism motor base is fixedly connected to a fourth support on the fixed base module; one end of the forceps opening and closing control mechanism lead screw is in interference fit with a bearing in the lead screw supporting seat, and the other end is connected to the forceps opening and closing control mechanism motor through the forceps opening and closing control mechanism coupler; the lead screw supporting seat is fixedly connected to a sixth support on the fixed base module; and one end of the second controller is movably connected to the lead screw through the screw nut, and the other end is connected to the forceps opening and closing control mechanism steel cable through a bearing.

7. The compound continuum robot for skull base tumor resection according to claim 1, further comprising a forceps rotation control mechanism, wherein the forceps rotation control mechanism comprises;

a forceps rotation control mechanism motor, a forceps rotation control mechanism belt tensioning adjusting bolt, a forceps rotation control mechanism belt tensioning adjusting bearing, a first forceps rotation control mechanism pulley and a second forceps rotation control mechanism pulley;

the forceps rotation control mechanism is fixedly connected to tor-base the concentric tube linear motion control mechanism motor base; the forceps opening and closing control mechanism steel cable is fixedly connected to the second forceps rotation control mechanism pulley; the first forceps rotation control mechanism pulley is fixedly connected to an output shaft of the forceps rotation control mechanism; and the first forceps rotation control mechanism pulley and the second forceps rotation control mechanism pulley are connected through a belt.

8. A method for controlling a compound continuum robot for skull base tumor resection, using the compound continuum robot for skull base tumor resection according to claim 1, and comprising: controlling a bending motion and a rotating motion of the notched continuum mechanism by the notched continuum control mechanism, controlling feeding and rotating motions of the concentric tube continuum mechanism by the concentric tube driving mechanism, and controlling feeding and rotating motions of the forceps opening and closing control mechanism steel cable by the forceps opening and closing control mechanism, such that forceps are opened or closed.

9. A method for controlling a compound continuum robot for skull base tumor resection, using the compound continuum robot for skull base tumor resection according to claim 2, and comprising: controlling a bending motion and a rotating motion of the notched continuum mechanism by the notched continuum control mechanism, controlling feeding and rotating motions of the concentric tube continuum mechanism by the concentric tube driving mechanism, and controlling feeding and rotating motions of the forceps opening and closing control mechanism steel cable by the forceps opening and closing control mechanism, such that forceps are opened or closed.

10. A method for controlling a compound continuum robot for skull base tumor resection, using the compound continuum robot for skull base tumor resection according to claim 3, and comprising: controlling a bending motion and a rotating motion of the notched continuum mechanism by the notched continuum control mechanism, controlling feeding and rotating motions of the concentric tube continuum mechanism by the concentric tube driving mechanism, and controlling feeding and rotating motions of the forceps opening and closing control mechanism steel cable by the forceps opening and closing control mechanism, such that forceps are opened or closed.

11. A method for controlling a compound continuum robot for skull base tumor resection, using the compound continuum robot for skull base tumor resection according to claim 4, and comprising: controlling a bending motion and a rotating motion of the notched continuum mechanism by the notched continuum control mechanism, controlling feeding and rotating motions of the concentric tube continuum mechanism by the concentric tube driving mechanism, and controlling feeding and rotating motions of the forceps opening and closing control mechanism steel cable by the forceps opening and closing control mechanism, such that forceps are opened or closed.

12. A method for controlling a compound continuum robot for skull base tumor resection, using the compound continuum robot for skull base tumor resection according to claim 5, and comprising: controlling a bending motion and a rotating motion of the notched continuum mechanism by the notched continuum control mechanism, controlling feeding and rotating motions of the concentric tube continuum mechanism by the concentric tube driving mechanism, and controlling feeding and rotating motions of the forceps opening and closing control mechanism steel cable by the forceps opening and closing control mechanism, such that forceps are opened or closed.

13. A method for controlling a compound continuum robot for skull base tumor resection, using the compound continuum robot for skull base tumor resection according to claim 6, and comprising: controlling a bending motion and a rotating motion of the notched continuum mechanism by the notched continuum control mechanism, controlling feeding and rotating motions of the concentric tube continuum mechanism by the concentric tube driving mechanism, and controlling feeding and rotating motions of the forceps opening and closing control mechanism steel cable by the forceps opening and closing control mechanism, such that forceps are opened or closed.

14. A method for controlling a compound continuum robot for skull base tumor resection, using the compound continuum robot for skull base tumor resection according to claim 9, and comprising: controlling a bending motion and a rotating motion of the notched continuum mechanism by the notched continuum control mechanism, controlling feeding and rotating motions of the concentric tube continuum mechanism by the concentric tube driving mechanism, and controlling feeding and rotating motions of the forceps opening and closing control mechanism steel cable by the forceps opening and closing control mechanism, such that forceps are opened or closed.

* * * * *